United States Patent [19]

Berthon-Jones et al.

[11] Patent Number: 5,560,354
[45] Date of Patent: Oct. 1, 1996

[54] FACIAL MASKS FOR ASSISTED RESPIRATION OR CPAP

[75] Inventors: Michael Berthon-Jones, Leonay; Michel Calluaud, Hunters Hill; Christopher E. Lynch, Turramurra; Kenneth F. Hely, Jannali, all of Australia

[73] Assignee: ResCare Limited, Australia

[21] Appl. No.: 262,134

[22] Filed: Jun. 17, 1994

[30] Foreign Application Priority Data

Jun. 18, 1993 [AU] Australia .................................. PL9490

[51] Int. Cl.$^6$ .......................... A62B 18/02; A61M 15/08
[52] U.S. Cl. .................. 128/205.25; 128/204.18; 128/206.24; 128/207.13; 128/205.24
[58] Field of Search .................. 128/205.25, 203.22, 128/206.24, 207.13, 206.28, 206.26, 204.18, 206.27, 207.11, 206.21, 207.12, 205.24, 206.29; 137/510; 251/61.1, 61.2

[56] References Cited

U.S. PATENT DOCUMENTS

| | | |
|---|---|---|
| 844,097 | 2/1907 | Randall . |
| 1,048,491 | 12/1912 | Butcher . |
| 1,139,850 | 5/1915 | Conkle ................................ 128/206.28 |
| 1,206,045 | 11/1916 | Smith . |
| 1,287,149 | 12/1918 | Walter et al. ....................... 128/206.28 |
| 1,635,275 | 7/1927 | Johnson . |
| 1,653,572 | 12/1927 | Jackson . |
| 1,873,160 | 8/1932 | Sturtevant . |
| 2,241,535 | 7/1939 | Bootby ..................................... 128/206 |
| 2,415,846 | 2/1947 | Randall ................................... 128/142 |
| 2,578,621 | 12/1951 | Yant ......................................... 128/146 |
| 2,765,788 | 10/1956 | Raiche .................................... 128/147 |
| 2,857,911 | 10/1958 | Bennett ................................. 128/147 |
| 2,931,356 | 4/1960 | Schwarz ................................ 128/146 |
| 3,330,273 | 7/1967 | Bennett ................................ 128/146.7 |
| 3,330,274 | 7/1967 | Bennett ................................ 128/146.7 |
| 3,608,574 | 9/1968 | Beaussant ............................. 251/61.1 |
| 3,658,058 | 4/1972 | Neidhart et al. ....................... 128/147 |
| 3,752,953 | 8/1973 | Girardina ................................ 219/137 |
| 3,763,862 | 10/1973 | Spieth .................................... 251/61.1 |
| 4,178,938 | 12/1979 | Au ......................................... 251/61.1 |
| 4,196,725 | 8/1980 | Gunderson ......................... 128/205.25 |

(List continued on next page.)

FOREIGN PATENT DOCUMENTS

| | | |
|---|---|---|
| 0462701A1 | 12/1991 | European Pat. Off. . |
| 492723 | 9/1938 | France . |
| 697762 | 9/1953 | France . |
| 775911 | 5/1957 | France . |
| 848215 | 9/1960 | France . |
| 1360632 | 7/1974 | France . |
| 207751 | 4/1907 | Germany . |
| 1104122 | 4/1961 | Germany . |
| 2115715 | 3/1971 | Germany . |
| 3707952A1 | 9/1988 | Germany . |

*Primary Examiner*—Edgar S. Burr
*Assistant Examiner*—William J. Deane, Jr.
*Attorney, Agent, or Firm*—Merchant, Gould, Smith, Edell, Welter & Schmidt, P.A.

[57] ABSTRACT

A combination mouth and nasal mask (40) for assisted respiration or CPAP is disclosed.

The combination mask (40) has a frame (42) to the rear side of which is mounted a separate nasal cushion (44) and mouth cushion (46). Both the nasal cushion (44) and the mouth cushion (46) separately form a rolled edge seal around the patient's face in the vicinity of the nose and in the vicinity of the lips. Inlet air is communicated from within the housing (48) to the mouth chamber, circumscribed by the mouth cushion (46) by means of one or more interconnecting tubes (62).

The proportion of air communicated to the mouth chamber (48) is controlled by the sizing and number of the tube(s), thus providing for free flow of air, restricted flow of air and pressure equalisation, or zero flow of air.

A mouth mask (10) for assisted respiration or CPAP also is disclosed.

18 Claims, 10 Drawing Sheets

U.S. PATENT DOCUMENTS

| | | | |
|---|---|---|---|
| 4,559,994 | 12/1985 | Waldmann | 165/41 |
| 4,573,464 | 3/1986 | Yo | 128/206.15 |
| 4,659,062 | 4/1987 | Mooney | 251/61.1 |
| 4,665,213 | 5/1987 | Alper | 560/105 |
| 4,782,832 | 11/1988 | Trimble et al. | 128/207.18 |
| 4,919,128 | 4/1990 | Kopala | 128/207.18 |
| 4,944,310 | 7/1990 | Sullivan | 128/848 |
| 5,018,519 | 5/1991 | Brown | 128/206.28 |
| 5,088,515 | 2/1992 | Kamen | 251/61.1 |
| 5,209,226 | 5/1993 | Goodley | 128/204.18 |
| 5,243,971 | 9/1993 | Sullivan | 128/205.25 |

FACIAL MASKS FOR ASSISTED RESPIRATION OR CPAP

TECHNICAL FIELD AND DISCUSSION OF THE PRIOR ART

The delivery of pressurised air or gas to the respiratory system of a patient is a requirement in several widely accepted medical treatments. These treatments include continuous positive airway pressure (CPAP) for people suffering from obstructive sleep apnea (OSA) and other breathing disorders during sleep, and for ventilation for people with various neuromuscular disorders that impede breathing. CPAP is also used in the treatment of lung disorders and in intensive care hospital use.

A description of CPAP treatment can be obtained from U.S. Pat. No. 4,944,310.

It has become increasingly popular to apply pressurised air or gas to the respiratory system through a nasal mask or nasal cannulae, in preference to a full face mask, although the passage of gas or air by the mouth would be a useful alternative in some circumstances. The increase in popularity of nasal masks is partly due to the ability to obtain a relatively airtight seal with a nasal mask, as less of the face has to be covered than with a fullface mask, and there is less relative movement around the nose than around the mouth where the mouth can open and the lower jaw droop. An example of a nasal mask, and of nasal CPAP treatment, is disclosed in U.S. Pat. No. 5,243,971.

Whilst the majority of patients who regularly use nasal CPAP when sleeping tolerate the nose mask quite well, there is a substantial minority who experience significant mouth leaks. There are other patients who are inveterate mouth breathers and for whom nasal CPAP simply is ineffective. These patients require CPAP treatment via the mouth in addition to, or instead of, the nose.

Mouth leaks may be partially a function of the treatment pressure, and may also relate to mouth and throat anatomical features of patients. Mouth leaks are undesirable for a number of reasons. They reduce the effect of pressure that is available to drive air into the lungs or to splint open the upper airway at the site of obstruction. This means that higher pressures have to be applied at the nose mask to compensate for the leak for the treatment to be effective. Mouth leaks also place an increased load on the nasal passages in drying the mucosal surfaces in the presence of a biased one-way flow, with some of the air entering through the nose passing straight out of the mouth. This can lead to unpleasant side effects including nasal obstruction, or a condition ranging from a runny to dry and stuffy nose and mouth after several hours of use. These side effects are often so severe that the patient is no longer able to tolerate treatment.

Nasal obstruction during sleep can make CPAP ineffective. A continual mouth leak can also cause an unpleasant odour to permeate a patient's room overnight. Mouth leaks also tend to be valve-like and not constant during inspiration and expiration, which makes it difficult for advanced diagnostic and control devices to function properly as they rely on accurate detection of a patient's respiratory flow.

Various solutions have been attempted to alleviate these problems. As noted, a full face mask can be used, but it is inherently difficult to obtain an airtight seal for reason of the patient's mouth and/or jaw moving during inspiration and expiration. Known full face masks have attempted to form a triangular shaped seal against the part of the face defined by the bridge of the nose, the two cheeks and the area between the bottom lip and chin.

The masks are secured by means of adjustable head straps. As previously noted, leaks nevertheless occur for reason of variation in facial topography around the nose and mouth; and because the mouth and lower jaw tend to move relative to the nose and upper lip. There is also a tendency for leaks to occur at the corners of the lips or the sides of the face where head strap tension is not acting in the direction best suited to effect the seal.

Various other methods, such as chin straps and plastic mouth guards placed between the lips and teeth, have been tried to prevent mouth leaks, but without real success.

DISCLOSURE OF THE INVENTION

In view of the foregoing considerations, the present invention discloses a mask for use in mouth ventilation or CPAP, the mask comprising a curved body portion to which is connected an inlet pipe for the supply of pressurised air or gas, a shaped mouth-surrounding cushion extending from the body portion and defining therewithin a chamber in fluid communication with the inlet pipe, and expiration means in fluid communication with the chamber, the body portion and the cushion thereof, in combination, being shaped to form a rolled edge seal circumscribing a region around the lips of a patient.

The invention further discloses a combination mouth and nose mask for use in ventilation or CPAP of the nose and mouth of a patient, the mask comprising a nasal cushion shaped to form a rolled edge seal circumscribing a region surrounding the patient's nose, a mouth cushion shaped to form a rolled edge seal circumscribing a region surrounding the patient's lips, the nasal cushion defining a nasal air supply chamber and the mouth cushion defining a mouth air supply chamber, the said nasal and mouth air supply chambers being commonly in fluid communication, and further in fluid communication with an inlet supply of pressurised air or gas, and expiration means, and wherein the mask is operable to supply pressurised air or gas for inspiration by the inlet to the said nasal and mouth chambers, and the expiration means provides for expiration by a route of either the mouth chamber in fluid communication with the nasal chamber, or by both chambers directly.

The invention further discloses a combination mouth and nose mask for use in ventilation or CPAP of the nose and mouth of a patient, the mask comprising a nasal cushion shaped to form a rolled edge seal circumscribing a region surrounding the patient's nose, a mouth cushion shaped to seal the patient's mouth, the nasal cushion defining a nasal air supply chamber and being in fluid communication with an inlet supply of pressurised air or gas, and expiration means, and wherein the mask is operable to supply pressurised air or gas for inspiration by the inlet to the nasal chamber, and the expiration means provides for expiration by the route of the nasal chamber.

The invention further discloses a safety valve for a mask used in ventilation or CPAP, the valve comprising a stretchable membrane formed within a chamber, the chamber having one or more openings to allow free passage of air from the atmosphere and an exiting opening in fluid communication with a breathing chamber of the mask, and whereby the membrane senses a pressure differential between pressurised air or gas supplied to a port means and the pressure of air or gas in the breathing chamber, and is displaced to seal the exiting opening when the air or gas in the breathing chamber is less than the pressure of air or gas supplied to the port means, and operable to open the exiting opening to a flow of air from the atmosphere when the air or gas in the breathing chamber is at a pressure greater than the pressure of air or gas supplied to the port means.

The invention yet further discloses a system for administering CPAP treatment by the mouth comprising:

a motor driven pump;

means for controlling delivery pressure of pressurised gas or air supplied by the pump;

a delivery pipe for delivery of gas or air from the pump; and a mask comprising a curved body portion to which the delivery pipe is connected, a shaped mouth-surrounding cushion extending from the body portion and defining therewithin a chamber in fluid communication with the delivery pipe, and expiration means in fluid communication with the chamber, the body portion and the cushion thereof, in combination, being shaped to form a rolled edge seal circumscribing a region around the lips of a patient.

The invention yet further discloses a system for administering CPAP treatment comprising:

a motor driven pump;

means for controlling the delivery pressure of pressurised gas or air supplied thereby;

a delivery pipe for delivery of pressurised gas or air from the pump; and a combination mouth and nose mask comprising a nasal cushion shaped to form a rolled edge seal circumscribing a region surrounding the patient's nose, a mouth cushion shaped to form a rolled edge seal circumscribing a region surrounding the patient's lips, the nasal cushion defining a nasal air supply chamber and the mouth cushion defining a mouth air supply chamber, the said nasal and mouth air supply chambers being commonly in fluid communication, and further in fluid communication with the delivery pipe, and expiration means, and wherein the mask is operable to supply pressurised air or gas for inspiration by the delivery pipe to the said nose and mouth chambers, and the expiration means provides for expiration by a route of either the mouth chamber in fluid communication with the nasal chamber, or by both chambers directly.

The invention yet further discloses a method of administering ventilation or CPAP comprising the steps of:

applying gas or air to a patient through a nasal mask continuously throughout the respiration cycle, the gas or air being at a pressure maintained to be greater than atmospheric pressure; and applying pressure equalising gas or air to a patient through a mouth mask continuously throughout the respiration cycle.

BRIEF DESCRIPTION OF THE DRAWINGS

Embodiments of the invention will now be described with reference to the accompanying drawings, in which.

DESCRIPTION OF PREFERRED EMBODIMENTS

Figure 1A:
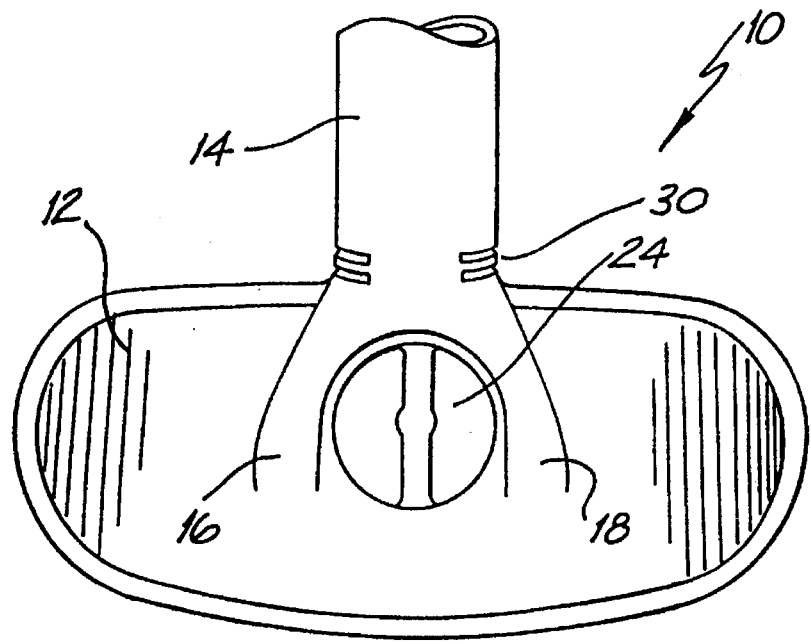
FIGS. 1a–1d respectively show front, side, inverted plan and rear views of a mouth mask.
Figure 1B:
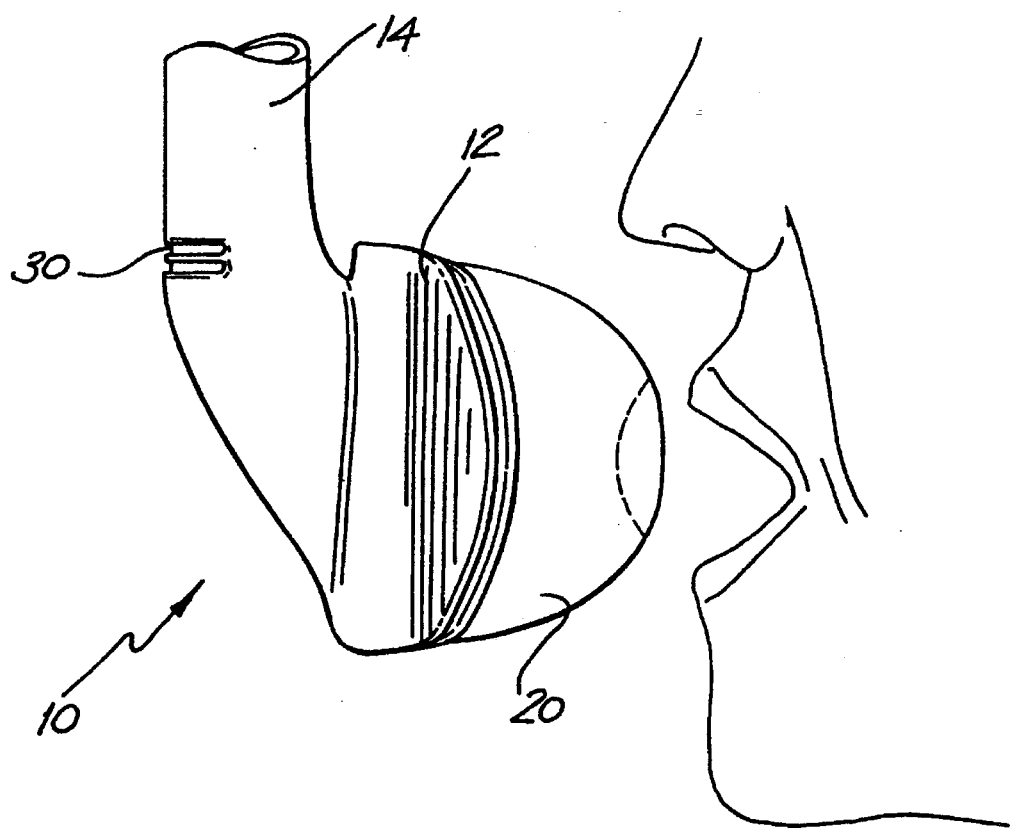

The mouth mask shown in FIGS. 1a and 1b is generally represented by the numeral 10. FIG. 1a is a front view of the mask 10, and FIG. 1b is a side view of the mask showing the operational relationship with the mouth of a patient to whom ventilation or CPAP is being administered.

Figure 1C:
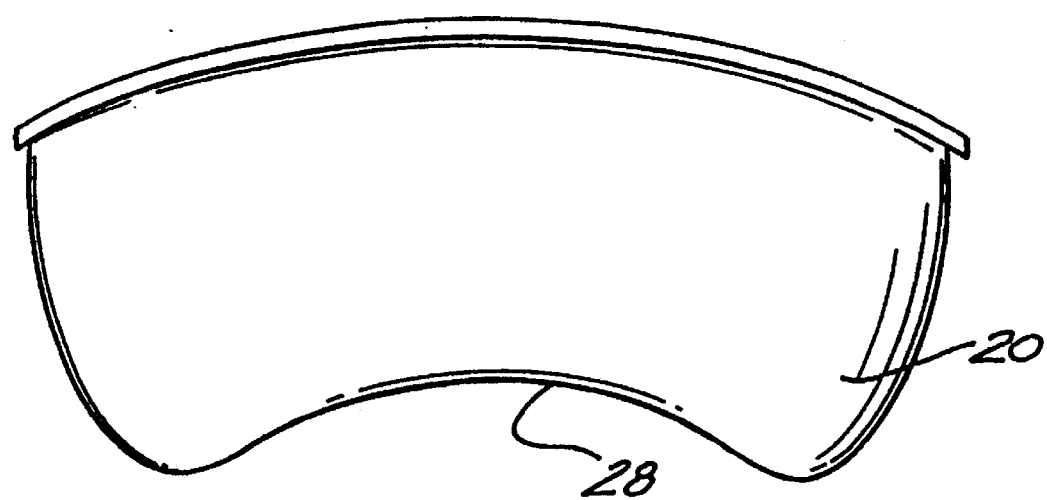
Figure 1D:
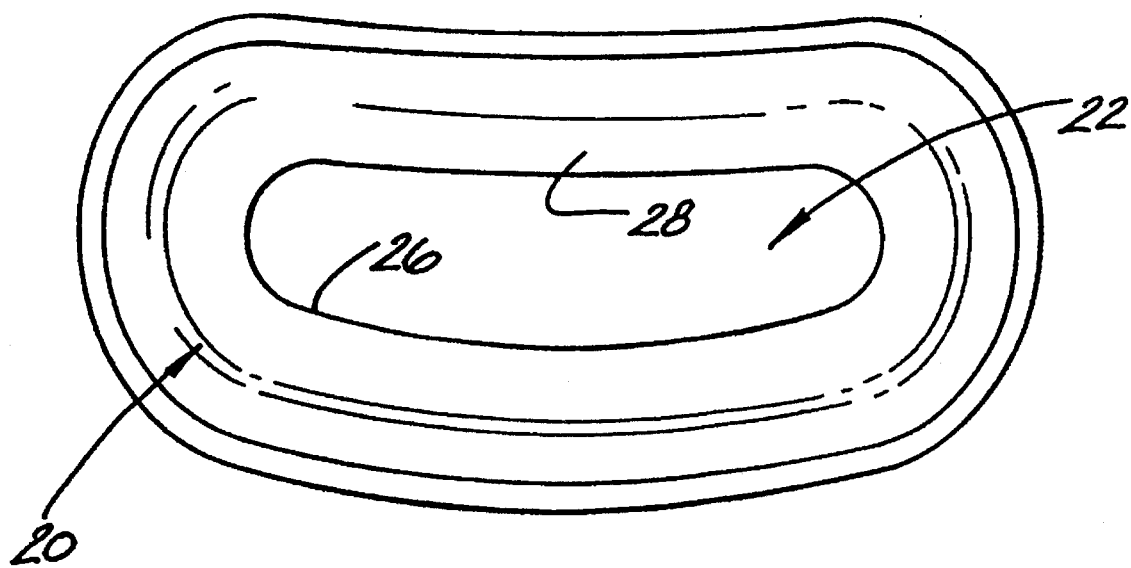

The mask 10 comprises a flared frame or plate 12, being gently curved with rounded ends. An inlet pipe 14, which ends in two branched passageways 16,18, is connected to the front of the plate 12. To the rear face of the frame 12 is connected a mouth cushion 20. The cushion 20 is 'banana' shaped, as can be best understood from the inverted plan view of FIG. 1c and rear view of FIG. 1d. The cushion 20 defines a chamber 22, which is in communication with the branched passageways 16,18, and, in turn, the inlet pipe 14. The closed-off end of the chamber 22, being a part of the frame 12, is provided with an optional safety valve 24, which operates to provide communication between the chamber 22 and the ambient air on there being negative pressure within the chamber 22 with respect to atmospheric pressure, such as may occur if the inlet pipe 14 becomes blocked and the patient inhales. In this regard, the valve 24 can be a conventional 'flap' valve. All of the component parts, save the mouth cushion 20 and the safety valve 24, are typically constructed of rigid plastics material.

In fitting the mouth mask 10 to a patient, the protruding end of the cushion 20 firstly comes in contact with the area surrounding the lips of the patient. The curved nature of the frame 12, together with the 'banana' shape of the cushion 20 ensures that the cushion 20 completely wraps around the patient's mouth. That region around the patient's lips deforms or depresses the surface of the cushion 20 forming a continuous rolled edged seal 28 therebetween. The patient's lips are accommodated inside the opening 26 to the cushion 20.

As the rolled edge 28 of the cushion 20 is not pre-formed or moulded into a particular shape, it forms a sealing rolled edge 28 on every occasion on which it is used, using the patient's face as a template to define the three-dimensional outline of the rolled edge. When not in use, the cushion 20 has no memory of where the rolled edge seal was previously formed, hence can adapt to different positions on the patient's face if slightly displaced, such as during sleeping. It is therefore also suitable for use by a number of different patients.

The part of the cushion 20 forming the rolled edge seal 28 can be made of a material such as moulded silicone rubber of a thickness between 0.15–0.5 millimeters. Typically, the rest of the mouth cushion 20 would be formed of thicker material having the necessary resiliency so that the cushion will not completely collapse when pressed against the face of the patient, nor billow out under high mask pressure. The use of silicon material has the advantages of being sufficiently transparent to enable a patient's mouth to be observed through the mask.

It is usual to provide fastening of the mouth mask to the head of the patient by means of head straps (not shown). The head straps must be tensioned to apply a positive sealing force for the cushion 20 at all points of contact with the patient's face.

In use of the mouth mask 10, air or gas under pressure is supplied to the inlet pipe 14, typically by a motor driven pump unit (not shown) and so passes to the mouth of the patient, providing the requisite positive airway pressure. The cushion 20 provides an airtight seal by virtue of the continuous rolled edge formed around the vicinity of the patient's lips. Internal air pressure acting normally on the rolled edge seal 28 against the patient's face counteracts the competing deleterious effect of this same internal pressure tending to force air out under the membrane around the inside edge of the orifice 26. This enables an airtight seal to be comfortably maintained at moderately high pressures, as may be applied in CPAP treatment or during ventilation (up to, say, 50 cm $H_2O$).

The greater the annular width of the rolled edge seal 28 around the patient's face, the less is the tendency for air to leak out of the mask. This also means that there is lesser point pressure applied to the patient's face by the tensioning head straps holding the mask in place. A further advantage of the rolled edge seal arrangement for the mouth cushion 20 is that if the mask 10 is disturbed during sleep, a seal immediately reforms along a new three-dimensional path defined by the line of contact between the area around the orifice 28 and the patient's face in the vicinity of the lips.

The mouth mask 10 can be used with the nasal passages blocked for delivery of CPAP or ventilation to a patient through the mouth. That is, there is a supply of positive air pressure, and that supplied air or gas under pressure is inspired by the patient and subsequently expired by means of the diffuser slots 30 or to another outlet to atmosphere which opens when the expired air/gas pressure exceeds atmospheric pressure.

The safety valve 24 is biased closed by a positive pressure in the mouth chamber 54 relative to the atmospheric pressure. The safety valve will be described in detail later with reference to FIGS. 7a and 7b.

Figure 2:
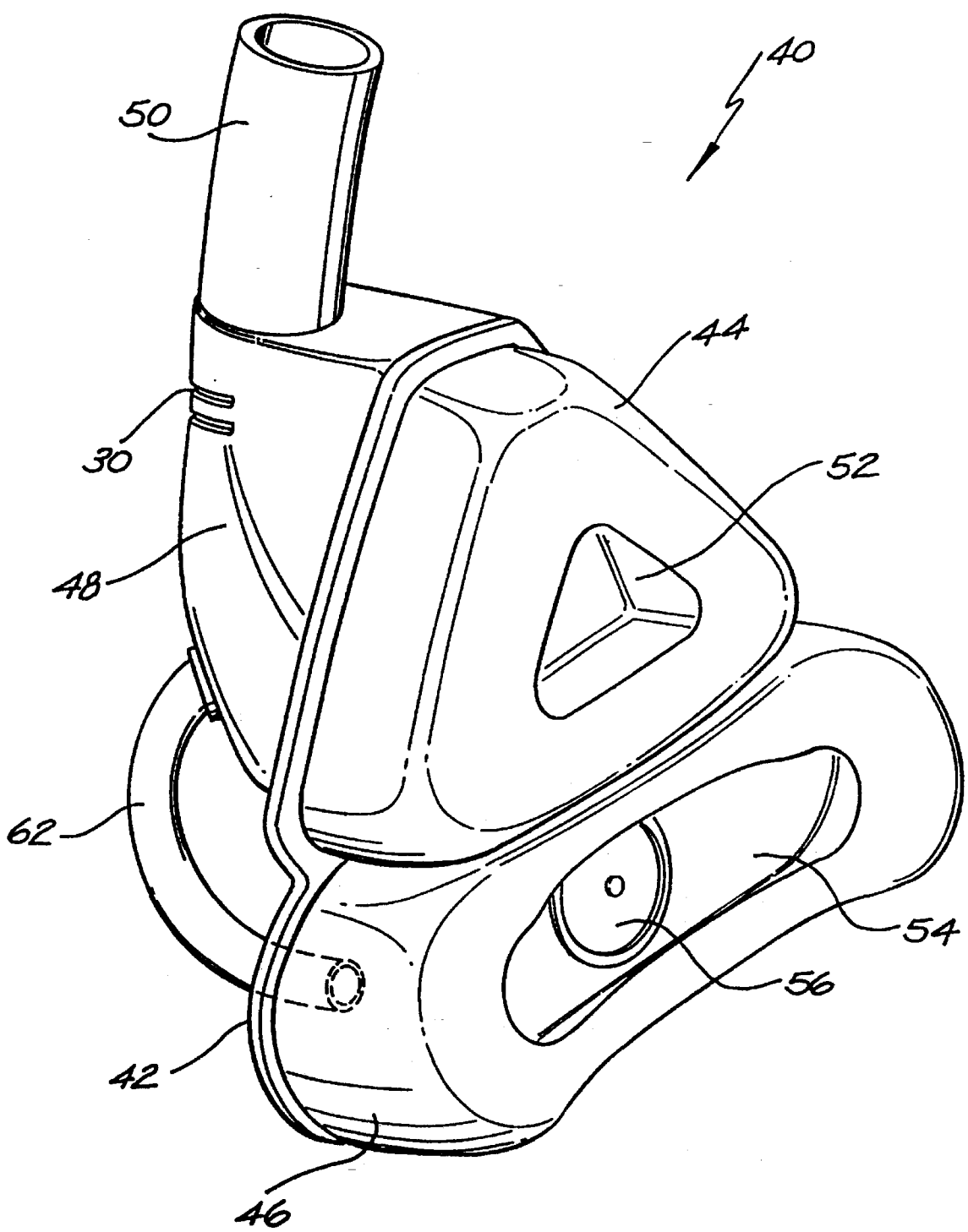
FIG. 2 shows a rear perspective view of a combination mouth and nasal mask.

FIG. 2 shows an embodiment of a composite nasal and mouth mask 40. The composite mask 40 has a frame 42 to the rear side of which is mounted a separate nasal cushion 44 and mouth cushion 46. The region of the frame 42 supporting the mouth cushion 46 is curved in the same manner as the frame 12 shown in FIG. 1a. The front side of the frame 42 is provided with a housing 48, to which is connected an inlet pipe 50 by which pressurised air or gas is supplied. Diffuser slots 30 are again provided for the purpose of expiration. The housing 48 forms a chamber in third communication with a nasal chamber 52 circumscribed by the nasal cushion 44. Inlet air is communicated from within the housing 48 to the mouth chamber 54, circumscribed by the mouth cushion 46, by means of one or more interconnecting tubes 62 (only one of which is shown) connecting to the housing 48.

The interconnecting tubes 62 provide for fluid communication between the housing 48 and the mouth chamber 54. The tubes 62 are sized differently for different applications i.e. in cross-sectional area and number. In a first case, they are sized to be large enough to allow the free passage of inlet air both to the nasal chamber 52 and the mouth chamber 54. This situation is well suited to CPAP treatment of a patient who will not breathe only through the mouth or only through the nose, hence requires both nasal and mouth CPAP treatment.

In a second case, the tubes 62 are sized to allow only enough air to pass to the mouth chamber 54 as would be required for pressure equalisation of the mouth chamber 54 in the absence of breathing through the mouth, thereby discouraging breathing through the mouth. The arrangement essentially allows only pressure equalisation, and very little volumetric flow by the mouth as compared with the nose (say 5 per cent).

In a third case, the interconnecting tubes 62 are not provided, hence there is no communication between the two chambers 52,54. In this way the mouth chamber 54 remains unpressurised except by air leakage from a patient's mouth which itself pressurises the mouth chamber preventing further leakage of air from the mouth. Thus it is the case that the patient himself pressurises the mouth chamber on opening his mouth, thus causing self-equilibration of pressure.

As with the embodiment of mouth mask shown in FIG. 1a, the enclosed end of the mouth chamber 54 is optionally provided with a safety valve 56.

In use of the composite mask 40, both the nasal cushion 44 and the mouth cushion 46 separately form a rolled edge seal, respectively around the patient's face in the vicinity of the nose and in the vicinity of the lips. Both the patient's nose and lips are contained within the nasal chamber 52 and mouth chamber 54 respectively with the composite mask 40 fitted. The mask can be secured to the patient's head by means of head straps (not shown). The head straps can be similar to those shown in published European application No. 0 549 299.

Whilst two cushions 44,46 have been shown, it is equally possible to construct the composite mask to be of a single cushion, yet still forming a separate nasal chamber and a separate mouth chamber. It that case, it may not necessary to provide the interconnecting tube(s) 62.

The composite mask 40 shown in FIG. 2 offers superior performance in the administration of assisted respiration or CPAP to that of the prior art. This is for the reason that the frame and mouth cushion are shaped to more correctly approximate the shape of the region around the lips. Further, the nose chamber and mouth chamber are decoupled, thus providing a support for the mouth from the top lip rather than at the bridge of the nose as is the case for the full face masks of the prior art. This arrangement, therefore, provides a superior seal against movement of the jaw during sleep, for example.

Figure 3A:
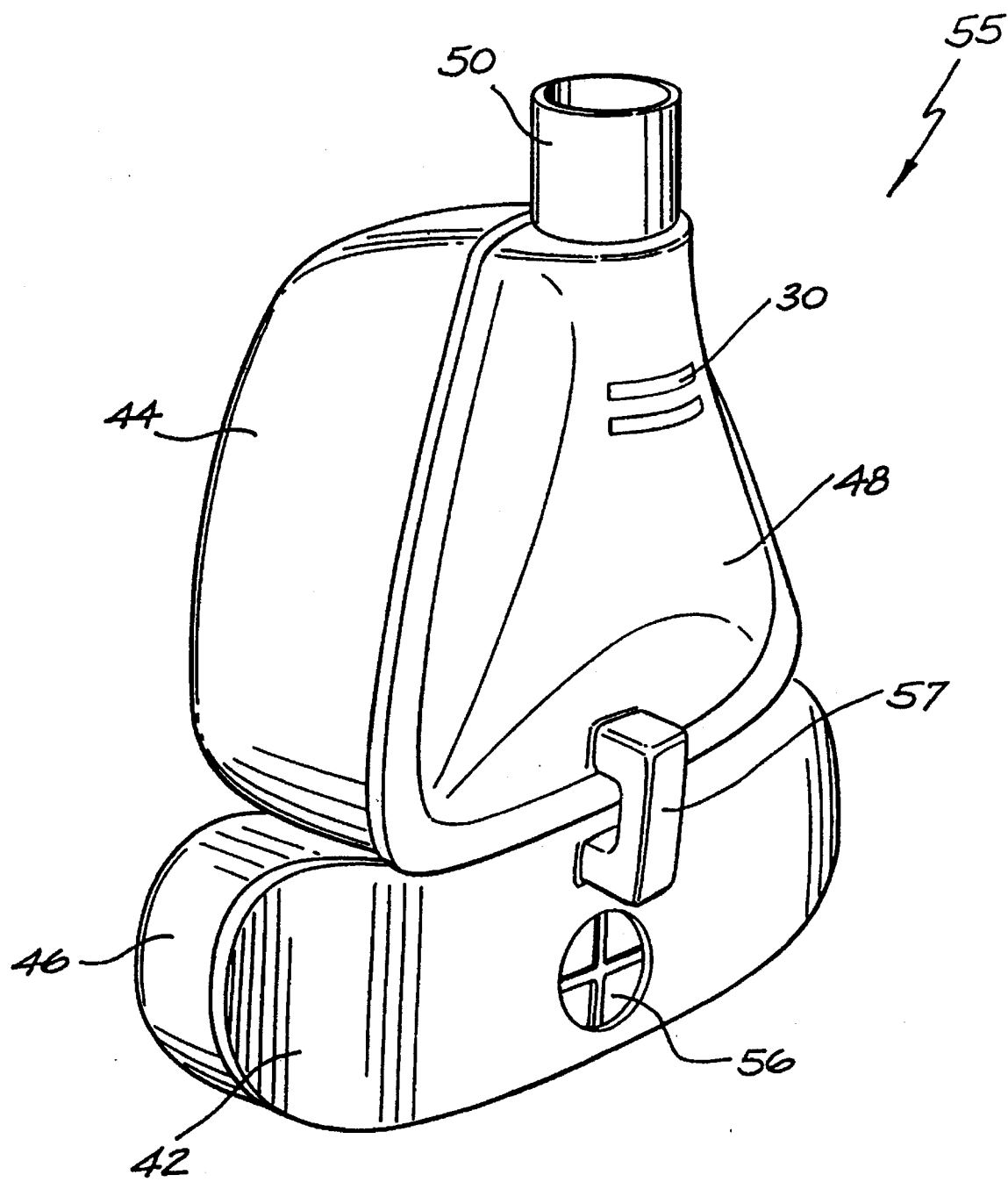
FIGS. 3a and 3b show a front perspective view of other embodiments of a combination mouth and nasal mask.
Figure 3B:
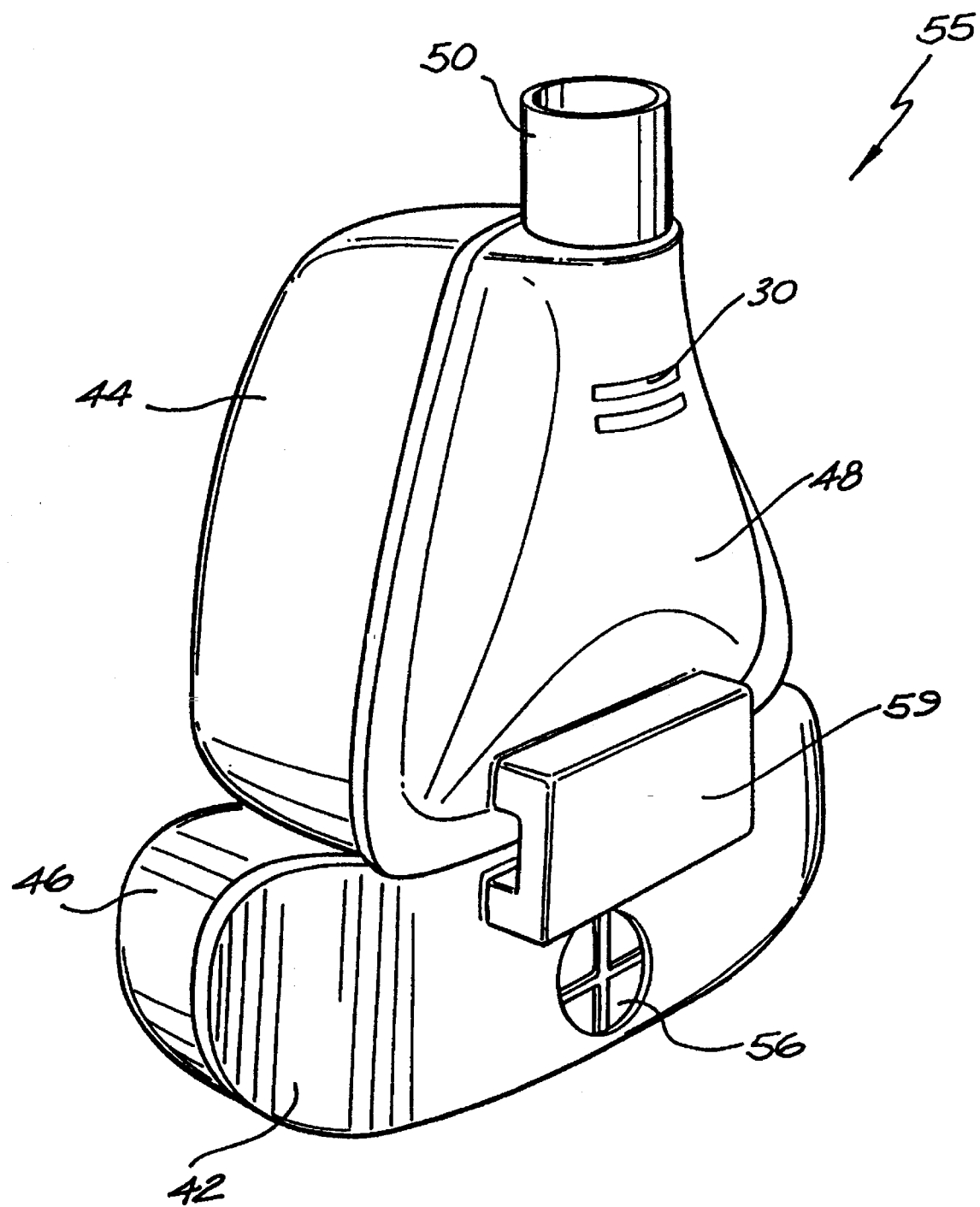

FIGS. 3a and 3b show front perspective views of another embodiment of a composite mask 55 that is similar to that shown in FIG. 2. Component parts common with the mask 40 are represented by the same reference numerals.

The mask 55 has a U-shaped duct 57,59 forming the communication between the chamber formed by the housing 48 and the mouth chamber 54 in place of the tube(s) 62. The cross-sectional area of the duct is adjusted in accordance with the desired relative flow required in the mouth chamber 54. FIG. 3a shows the duct 57 to be of smaller cross-sectional area than the duct 59 shown in FIG. 3b, hence the embodiment of FIG. 3a allows a lesser volumetric flow between the respective chambers.

Figure 4A:
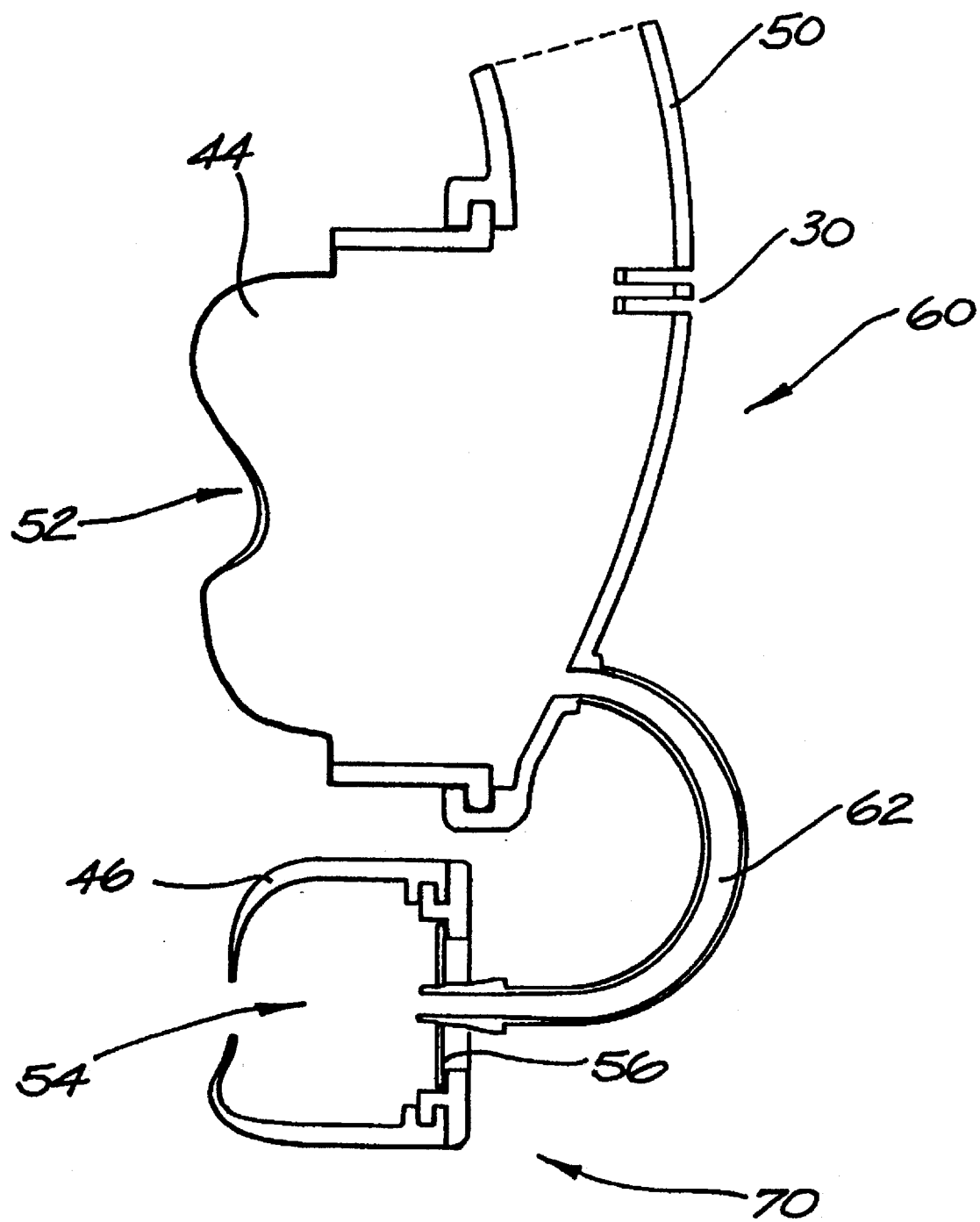
FIG. 4a shows a vertical sectional side view of a further embodiment of a combination mouth and nasal mask.

FIG. 4a shows a variation of the composite mask 40 as described above with reference to FIG. 2. In this instance, separate nose and mouth masks 60,70 are provided, otherwise like-numbered integers as discussed in relation to FIG. 2 are also used in FIG. 4a. The mouth mask 70 is again connected with the nose mask 60 by means of the interconnecting tube(s) 62, thus providing the pressure equalisation between the respective nasal chamber 52 and mouth chamber 54. Use of the 'composite mask' formed by the nose mask 60 and mouth mask 70 is otherwise the same as for the composite mask 40 shown in FIG. 2.

Figure 4B:
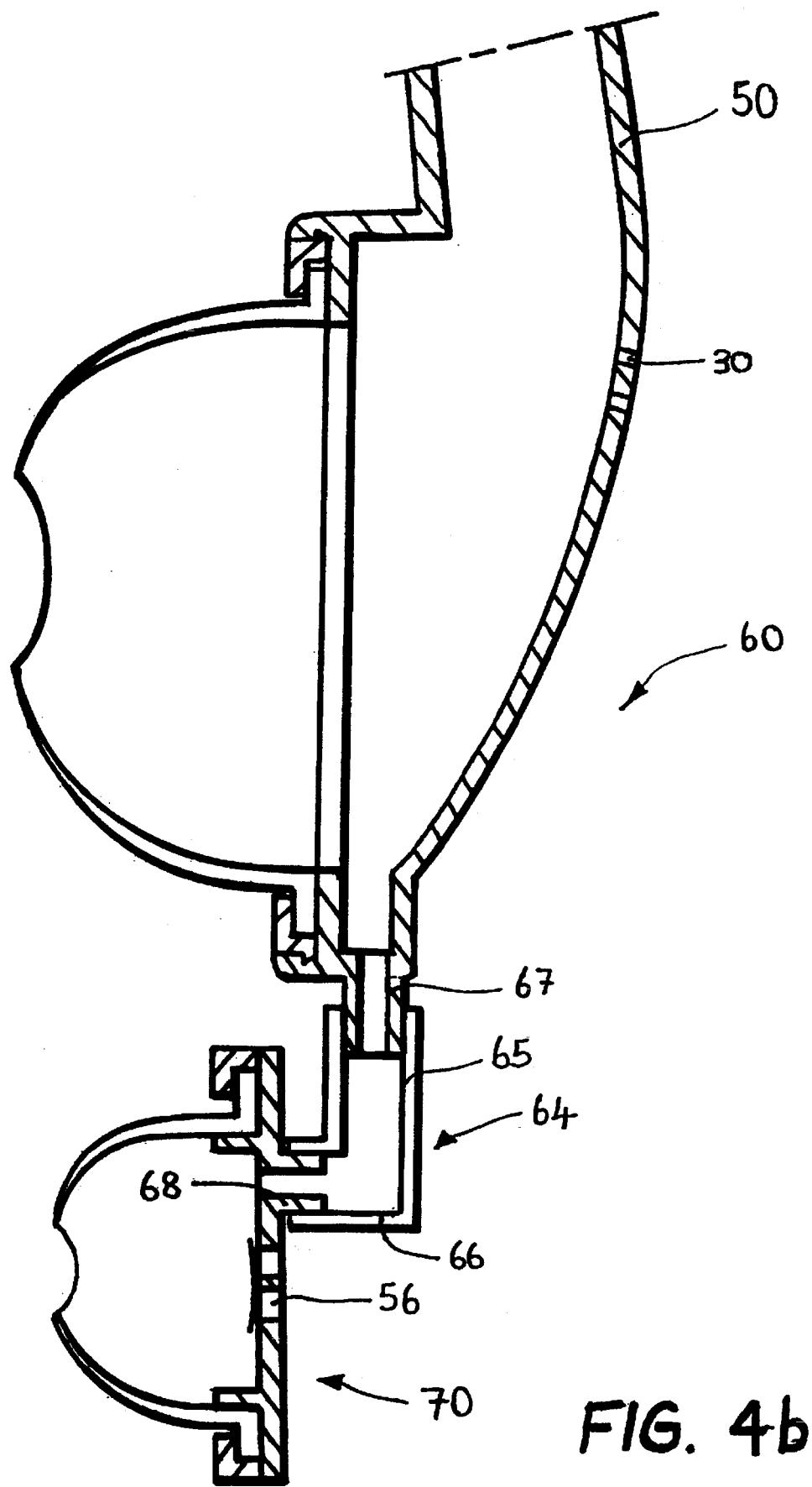
FIG. 4b shows a vertical sectional side view of a yet further embodiment of a combination mouth and nasal mask.

The interconnecting tube(s) 62 can be replaced by an L-shaped duct 64 as shown in FIG. 4b. The duct 64 is generally equivalent to either one of the ducts (57,59) shown in FIGS. 3a and 3b. The legs 65,66 securely slidingly engage respective extended ports 67,68 in the nose mask 50 and the mouth mask 70. The safety valve 56 is separate from the port 68, in contra-distinction to the arrangement shown in FIG. 4a. The legs 65,66 of the duct are trimmed to provide the optimal fitting for individual patients, both in respect of vertical and horizontal relative displacement of the nose mask 60 and the mouth mask 70. The duct 64 must be made of material that has flexibility to cater for the relative location of the mouth mask 70 with respect to the nose mask 60 when in use, and yet resists collapse or restriction of the fluid path.

Figure 5:
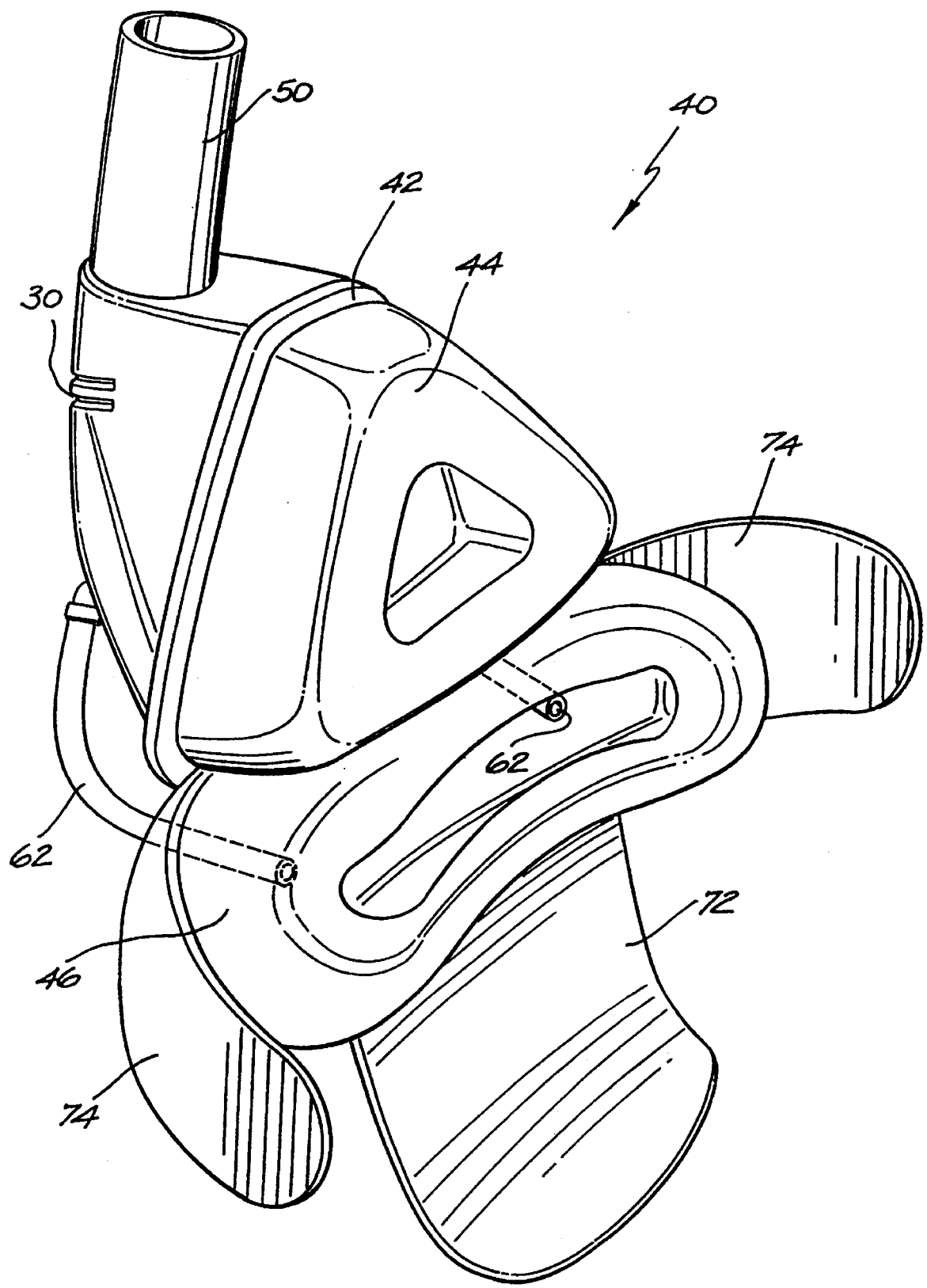
FIG. 5 shows a rear perspective view of another embodiment of a combination mouth and nasal mask.

FIG. 5 shows the composite mask 40 of FIG. 2, further adapted for security and ease of fitting to a patient's face. A contoured wrap-around chin plate 72 is attached to the frame 42, and fits under the patient's chin when worn. Two cheek plates 74 are also provided, and wrap-around the side of the face in the region of the cheeks, thereby further assisting in holding the mouth mask 70 in place ensuring that the mouth cushion 46 seal is maintained around the patient's lips, especially at the corners which can otherwise be problematically for leaks for 'longer' mouths. The chin and cheek plates typically are formed from a mouldable thermoplastics material such as polycarbonate, hence can be tailored to suit a patient's facial anatomy. The cheek plates 74 can also have head straps (not shown) fixed thereto, passing around the sides of a patient's face and behind their neck.

Figure 6:
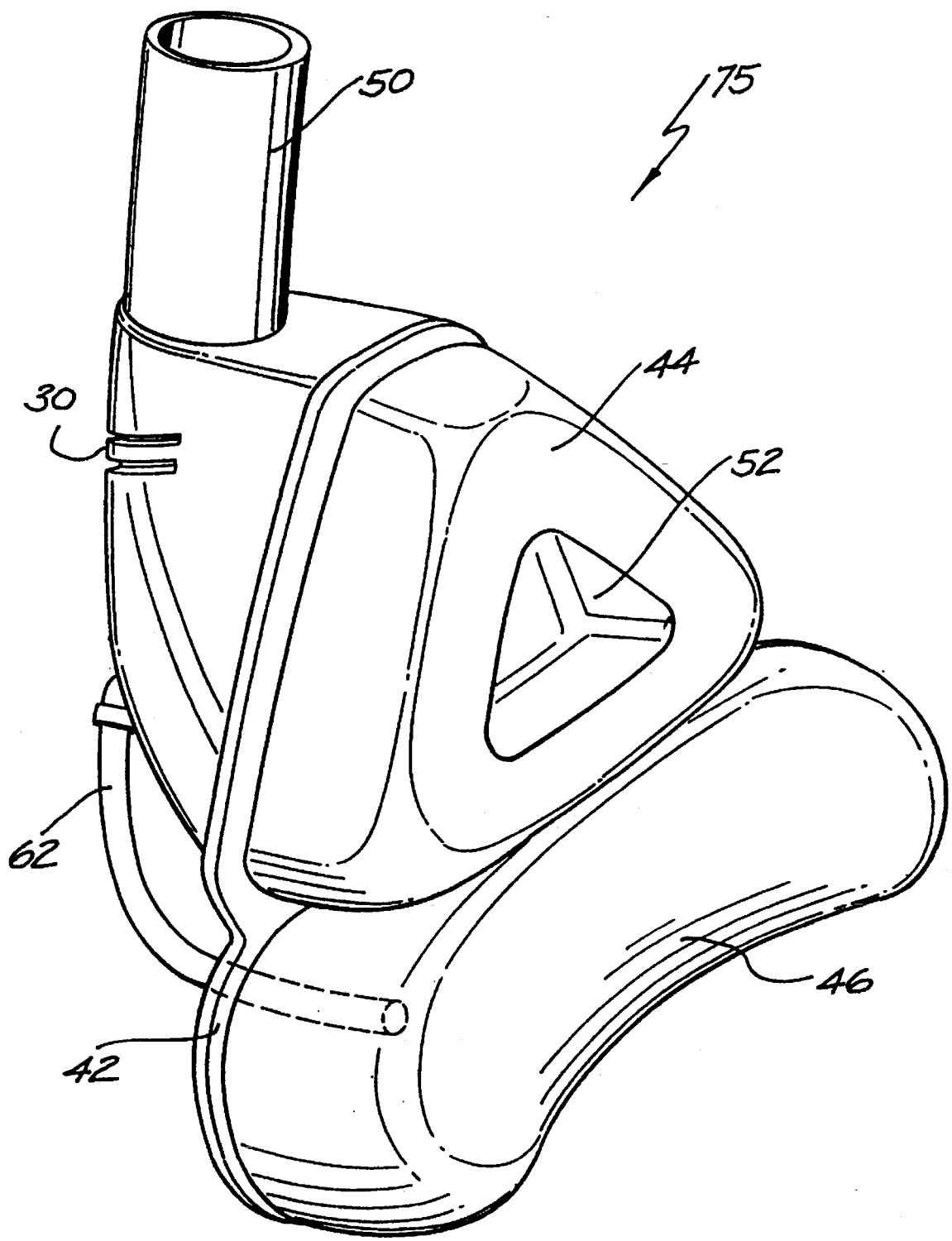
FIG. 6 shows, as a perspective view, another embodiment of a composite mask with a closed mouth seal.

FIG. 6 shows a further embodiment of a composite mask 75 intended to be used for ventilation or CPAP where the patient is to be actively discouraged from breathing via the mouth. In this regard, the mask 75 again resembles the composite nose mask 40 as shown in FIG. 2, but has the mouth chamber 54 blocked off to form a mouth gag. The mouth cushion 46 is pressurized by the supply air provided by the interconnecting tube(s) 62. The patient is required to inspire and expire only by the nose, any mouth breathing is positively discouraged by means of the mouth being blocked-off.

The mask 75 is utilised where a patient has particular difficultly with mouth leaks, and would otherwise experience the problems or complications associated with such a condition, in which case breathing from the mouth is to be prevented completely.

Figure 7A:
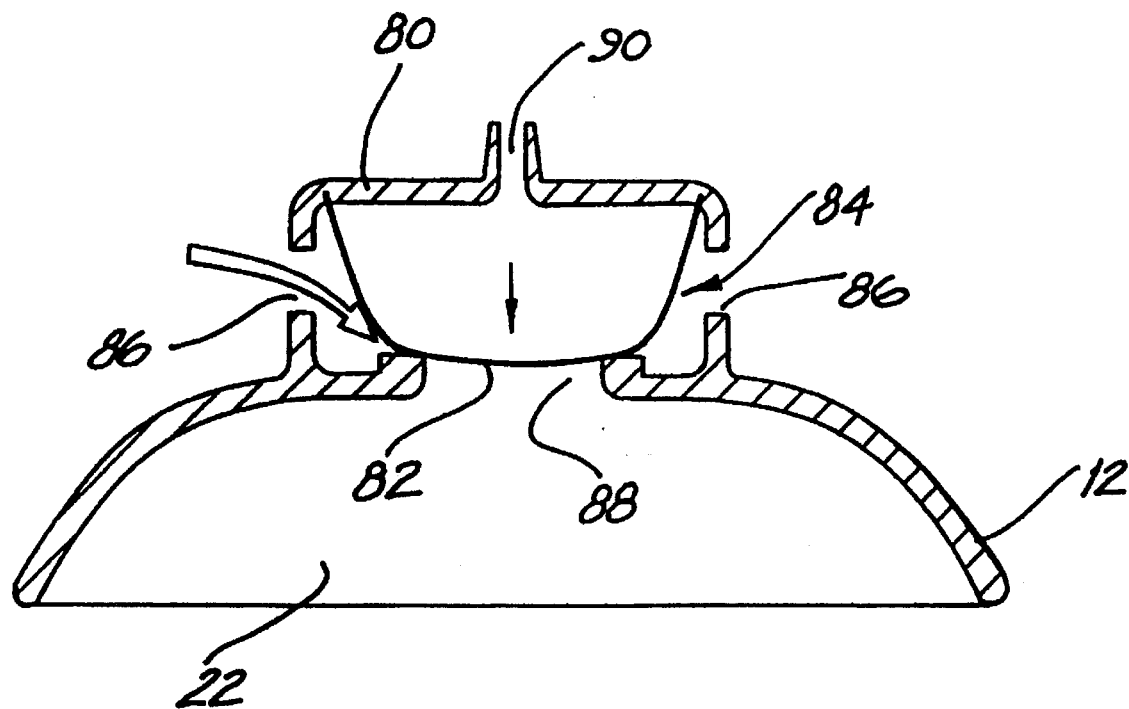
FIGS. 7a and 7b show, in cross-sectional form, an active safety valve.
Figure 7B:
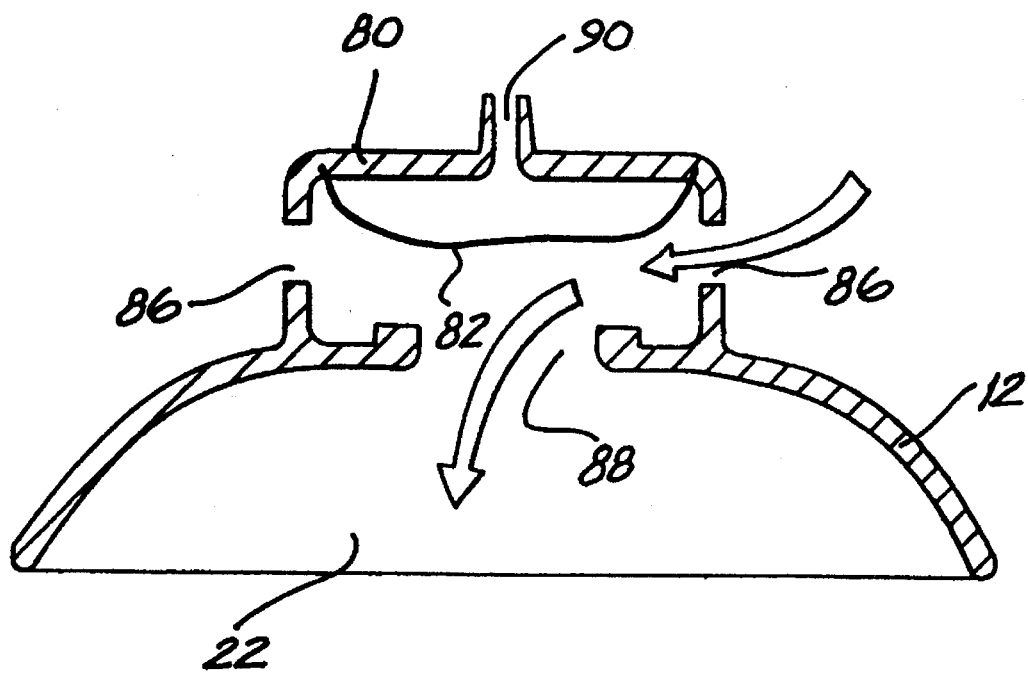

FIGS. 7a and 7b show an embodiment of the active safety valve 80 that can be substituted for the 'flap' valve embodiments 24,56 previously described. Operation of the safety valve 80 conveniently will be described with respect to the mouth mask 10 shown in FIGS. 1a and 1b, absent the mouth cushion 20. That is, it is to be assumed the mouth cushion 20 has sealed against the lips of the patient, in which case the (breathing) chamber 22 is closed-off and the mouth mask 10 is in use.

The purpose of the active safety valve 80 is to ensure that if the supply of air to the inlet pipe 14 from the motor driven pump unit ceases for some reason, the patient can still inhale and exhale air from the atmosphere. The active safety valve 80 comprises a thin stretchable elastomeric cup-shaped membrane 82 formed within a chamber 84. The chamber 84 has one or more openings 86 to allow the passage of air from the atmosphere, and an exiting opening 88 in communication with the chamber 22. The membrane 82 senses pressure of a supply of air generated at the motor driven pump unit by means of a port 90 in fluid communication with the pump unit via a separate conduit (not shown). This pressure of supply of air to the port 90 is arranged such that it is always greater than the pressure in the breathing chamber 22. Furthermore, the pump unit is arranged such that whenever the pressure of air within the breathing chamber 22 falls to atmospheric, the pressure of air at the port 90 and sensed by the membrane 82 also falls to atmospheric.

Under normal conditions, the pressure being supplied to the port 90, and hence acting on the membrane 82, is greater than the pressure of air in the chamber 22, in which case the membrane 82 is displaced downwardly to seal off the exiting opening 88, thus blocking off the ingress of air from the atmosphere. In the event that pump unit fails the membrane 82 is caused to be displaced upwardly, thereby opening the exiting openings 88 to the flow of atmospheric air into the chamber 22. The patient can also exhale via the opened valve, as the positive pressure of expiration does not force the membrane 82 downward; that is only achieved on the re-establishment of supply air through the port 90. A particular advantage of this valve over conventional valve is that it does not require respiration to operate, which is a situation encountered during apneic episodes.

In a further embodiment, the safety valve 80 can be held closed pneumatically, electrically or mechanically. On a power failure or stoppage of the source of pressurized gas via the inlet pipe 14, those mechanisms are caused to allow the flow of air to and from atmosphere on respiration.

All of the masks previously described can be utilised in CPAP apparatus, which, as a system, comprises a motor driven pump unit that is controllable to provide a flow of air at a pressure above atmospheric (e.g. in the range of about 4 to 16 cm $H_2O$) via a flexible conduit or tube to the mask.

What we claim is:

1. A combination mouth and nose mask for use in ventilation or CPAP of the nose and mouth of a patient, the mask comprising a separate nasal cushion and mouth cushion, the nasal cushion shaped to form a rolled edge seal circumscribing a region surrounding the patient's nose, the mouth cushion shaped to form a rolled edge seal circumscribing a region surrounding the patient's lips, the nasal cushion defining a nasal air supply chamber and the mouth cushion defining a mouth air supply chamber, the said nasal and mouth air supply chambers being commonly in fluid communication, and further in fluid communication with an inlet supply of pressurised air or gas, and expiration means, a safety valve comprising a valve chamber and a stretchable membrane formed within said valve chamber, said valve chamber having one or more openings to allow free passage of air from the atmosphere and an exit opening in fluid communication with said mouth chamber, and wherein the mask is operable to supply pressurized air or gas for inspiration by the inlet to the said nasal and mouth chambers, and the expiration means provides for expiration by a route of either the mouth chamber in fluid communication with the nasal chamber, or by both chambers directly.

2. A combination nose and mouth mask as claimed in claim 1, wherein the chambers are interconnected by communication means whose pneumatic impedance is selectively chosen to allow the free passage of inlet air between the two chambers as would be required for pressure equalization of the mouth chamber in the absence of breathing through the mouth.

3. A combination nose and mouth mask as claimed in claim 2, wherein the communication means is a duct.

4. A combination nose and mouth mask as claimed in claim 1, wherein the nasal cushion and the mouth cushion are carried on separate body portions.

5. A combination nose and mouth mask as claimed in any one of the claims 1, 2, 3 or 4, further comprising a safety valve comprising a valve chamber and a stretchable membrane formed within said valve chamber, said valve chamber having one or more openings to allow free passage of air from the atmosphere and an exiting opening in fluid communication with said mouth chamber, said membrane being a fluid communication with a port means which is in fluid communication with said inlet pipe, and the pressure of gas at said port means being greater than the pressure in said valve chamber, whereby said membrane is elastically displaced to seal said exiting opening, and further operable to open said exiting opening to a flow of air from the atmosphere by elastic restoration when the pressure at said port means and the pressure in said valve chamber both fall to or below atmospheric pressure.

6. A combination nose and mouth mask as claimed in claim 5 further comprising a contoured chin-plate and cheek plates connected with the body portion to fix the mask to the patient's face by wrapping around the chin and cheek areas thereof.

7. A combination nose and mouth mask as claimed in claim 2, wherein the communication means is one or more tubes.

8. A combination nose and mouth mask as claimed in claim 1, wherein each of said nasal cushion and said mouth cushion have a first region constructed of a material having a thickness that enables ready deformation, and a second region constructed of the same material as said first region but having a thickness that is resilient to avoid collapse of each respective said cushion in the absence of supplied pressurized air.

9. A combination nose and mouth mask as claimed in claim 1, wherein the chambers are interconnected by communication means whose pneumatic impedance is selectively chosen to allow only enough air to pass to the mouth chamber as would be required for pressure equalization of the mouth chamber in the absence of breathing through the mouth.

10. The mask of claim 8 comprising an attachment means for releasably fastening the mask to a patient's head.

11. A combination mouth and nose mask for use in ventilation or CPAP of the nose and mouth of a patient, the mask comprising a nasal cushion shaped to form a rolled edge seal circumscribing a region surrounding the patient's nose, a mouth cushion shaped to seal the patient's mouth, the nasal cushion defining a nasal air supply chamber and being in fluid communication with an inlet supply of pressurized air of gas, and expiration means, and wherein the mask is operable to supply pressurized air or gas inspiration by the inlet to the nasal chamber and the expiration means provides for expiration by the route of the nasal chamber a safety chamber comprising a valve chamber and a stretchable membrane formed within said valve chamber, said valve chamber having one more openings to allow free passage of air from the atmosphere and an exit opening in fluid communication with said mouth chamber.

12. A safety valve for a mask used in ventilation or CPAP, the valve comprising a stretchable membrane formed within a valve chamber, said valve chamber having one or more openings to allow free passage of air from the atmosphere and an exiting opening in fluid communication with a mouth chamber, said membrane being in fluid communication with a port means which is in fluid communication with an inlet pipe, and the pressure of gas at the port means being greater than the pressure in said valve chamber, whereby said membrane is elastically displaced to seal said exiting opening, and further operable to open said exiting opening to a flow of air from the atmosphere by elastic restoration when the pressure at said port means and the pressure in said valve chamber both fall to or below atmospheric pressure.

13. A safety valve as claimed in claim 12, further comprising a frame-like housing for the membrane, and wherein the membrane is cup-shaped and anchored to the housing.

14. A safety valve as claimed in claim 13, wherein the membrane is constructed of thin stretchable elastomeric material.

15. A system for administering CPAP treatment comprising:

a motor driven turbine;

means for controlling the delivery pressure of pressurized gas or air supplied thereby;

a delivery pipe for delivery of pressurized gas or air from the turbine; and a combination mouth and nose mask comprising a separate nasal cushion and mouth cushion, the nasal cushion shaped to form a rolled edge seal circumscribing a region surrounding the patient's nose, the mouth cushion shaped to form a rolled edge seal circumscribing a region surrounding the patient's lips, the nasal cushion defining a nasal air supply chamber and the mouth cushion defining a mouth air supply chamber, a safety valve mounted in said mouth air supply chamber, the said nasal and mouth air supply chambers being commonly in fluid communication, and further in fluid communication with the delivery pipe, and expiration means, and wherein the mask is operable to supply pressurized air or gas for inspiration by the delivery pipe to said nose and mouth chambers, and the expiration means provided for expiration by a route of either the mouth chamber in fluid communication with the nasal chamber, or by both chambers directly.

16. A system as claimed in claim 15, wherein the chambers are interconnected by communication means whose pneumatic impedance is selectively chosen to allow the free passage of inlet air between the two chambers.

17. A CPAP system as claimed in claim 16, said a safety valve comprising a stretchable membrane formed within a valve chamber, said valve chamber having one or more openings to allow free passage of air from the atmosphere and an exiting opening in fluid communication with said mouth chamber, a port means in fluid communication with said inlet pipe said membrane being in fluid communication with said port means, and the pressure of gas at said port means being greater than the pressure in said valve chamber, whereby said membrane is elastically displaced to seal said exiting opening, and further operable to open said exiting opening to a flow of air from the atmosphere by elastic restoration when the pressure at said port means and the pressure in said valve chamber both fall to or below atmospheric pressure.

18. A system as claimed in claim 15, wherein the chambers are interconnected by communication means whose pneumatic impedance is selectively chosen to allow only enough air to pass to the mouth chamber as would be required for pressure equalization of the mouth chamber in the absence of breathing through the mouth.

* * * * *